(12) United States Patent
Lee et al.

(10) Patent No.: US 9,393,013 B2
(45) Date of Patent: Jul. 19, 2016

(54) TOOLS FOR FIBER REINFORCED ANTI-COMPRESSIVE ADHERENT SUTURE METHOD

(76) Inventors: Heeyoung Lee Lee, Gusan (KR); Hyun-jin Yang, Seoul (KR)

(*) Notice: Subject to any disclaimer, the term of this patent is extended or adjusted under 35 U.S.C. 154(b) by 1032 days.

(21) Appl. No.: 12/599,348

(22) PCT Filed: May 8, 2007

(86) PCT No.: PCT/KR2007/002263
§ 371 (c)(1),
(2), (4) Date: Mar. 31, 2010

(87) PCT Pub. No.: WO2008/136549
PCT Pub. Date: Nov. 13, 2008

(65) Prior Publication Data
US 2010/0241141 A1    Sep. 23, 2010

(51) Int. Cl.
*A61B 17/10* (2006.01)
*A61B 17/06* (2006.01)
*A61B 17/24* (2006.01)
*A61B 17/00* (2006.01)

(52) U.S. Cl.
CPC ........... *A61B 17/06166* (2013.01); *A61B 17/24* (2013.01); *A61B 2017/00792* (2013.01); *A61B 2017/06176* (2013.01)

(58) Field of Classification Search
CPC ............... A61B 17/06166; A61B 2017/06176; A61B 2017/00792
See application file for complete search history.

(56) References Cited

U.S. PATENT DOCUMENTS

| | | | | |
|---|---|---|---|---|
| 962,218 A * | 6/1910 | Heitz-Boyer | ................. | 606/146 |
| 1,087,845 A * | 2/1914 | Stevens | ...................... | 604/159 |
| 2,737,954 A * | 3/1956 | Knapp | ......................... | 606/146 |
| 2,808,055 A * | 10/1957 | Thayer | .......................... | 606/144 |
| 3,013,559 A * | 12/1961 | Thomas | ........................ | 606/146 |
| 3,123,077 A * | 3/1964 | Alcamo | ......................... | 606/228 |
| 3,186,262 A * | 6/1965 | Parstorfer | .................. | 140/93 R |
| 3,835,854 A * | 9/1974 | Jewett | .......................... | 604/159 |
| 4,935,027 A * | 6/1990 | Yoon | ............................. | 606/146 |
| 5,342,376 A * | 8/1994 | Ruff | ............................... | 606/151 |
| 5,346,498 A * | 9/1994 | Greelis et al. | ................ | 606/108 |
| 5,425,747 A * | 6/1995 | Brotz | ............................. | 606/228 |
| 5,643,292 A * | 7/1997 | Hart | ............................... | 606/144 |
| 5,919,199 A * | 7/1999 | Mers Kelly et al. | .......... | 606/139 |
| 5,931,855 A * | 8/1999 | Buncke | ........................ | 606/228 |
| 5,944,724 A * | 8/1999 | Lizardi | .......................... | 606/104 |
| 6,241,747 B1 * | 6/2001 | Ruff | ............................... | 606/216 |
| 6,270,517 B1 * | 8/2001 | Brotz | ............................ | 606/228 |

(Continued)

*Primary Examiner* — Gregory Anderson
*Assistant Examiner* — Son Dang
(74) *Attorney, Agent, or Firm* — John K. Park; Park Law Firm

(57) ABSTRACT

Disclosed therein are instruments necessary for a surgical operation performed to keep a length of lengthened tissues, for instance, a raised nose on the face, using an improved thread embedded in a living body. More particularly, the present invention provides instruments for a fiber reinforced anti-compressive adherent suture method used to lengthen or separate soft tissues in the living body, which includes a tissue-implantable thread inserted into the living body by an injector needle and having wedge-shaped protrusions of different directionalities formed in two sections thereof, an injector for inserting the injector needle into the living body and moving it forwardly and backwardly, an instrument for inserting the tissue-implantable thread into the injector, and an instrument for vertically splitting an end of the thread to make the thread act in the living body.

6 Claims, 8 Drawing Sheets

(56) References Cited

U.S. PATENT DOCUMENTS

| | | | |
|---|---|---|---|
| 6,780,198 B1* | 8/2004 | Gregoire et al. | 606/232 |
| 7,226,468 B2* | 6/2007 | Ruff | 606/216 |
| 7,311,715 B2* | 12/2007 | Sauer et al. | 606/148 |
| 7,749,236 B2* | 7/2010 | Oberlaender et al. | 606/148 |
| 8,100,940 B2* | 1/2012 | Leung et al. | 606/228 |
| 2003/0149447 A1* | 8/2003 | Morency et al. | 606/228 |
| 2004/0060409 A1* | 4/2004 | Leung et al. | 83/522.14 |
| 2004/0060410 A1* | 4/2004 | Leung et al. | 83/522.14 |
| 2004/0088003 A1* | 5/2004 | Leung et al. | 606/228 |
| 2005/0165417 A1* | 7/2005 | Sauer et al. | 606/144 |
| 2005/0267531 A1* | 12/2005 | Ruff et al. | 606/228 |
| 2005/0283171 A1* | 12/2005 | Bellafiore et al. | 606/144 |
| 2007/0005109 A1* | 1/2007 | Popadiuk et al. | 606/228 |
| 2007/0005110 A1* | 1/2007 | Collier et al. | 606/228 |
| 2007/0208355 A1* | 9/2007 | Ruff | 606/139 |
| 2008/0312688 A1* | 12/2008 | Nawrocki et al. | 606/228 |
| 2009/0012560 A1* | 1/2009 | Hunter et al. | 606/228 |
| 2009/0210003 A1* | 8/2009 | Sulamanidze et al. | 606/228 |
| 2009/0210006 A1* | 8/2009 | Cohen et al. | 606/232 |
| 2010/0298637 A1* | 11/2010 | Ruff | 600/104 |
| 2011/0046668 A1* | 2/2011 | Goraltchouk et al. | 606/228 |
| 2011/0046669 A1* | 2/2011 | Goraltchouk et al. | 606/228 |
| 2012/0116449 A1* | 5/2012 | Kirsch et al. | 606/228 |
| 2012/0172931 A1* | 7/2012 | Ben Rubi | 606/228 |

* cited by examiner (a)                    (b)

TOOLS FOR FIBER REINFORCED ANTI-COMPRESSIVE ADHERENT SUTURE METHOD

TECHNICAL FIELD

The present invention relates to instruments necessary for a surgical operation performed to keep a length of lengthened tissues, for instance, a raised nose on the face, using an improved thread embedded in a living body, more particularly, to instruments for a fiber reinforced anti-compressive adherent suture method used to lengthen or separate soft tissues in the living body, which includes a tissue-implantable thread having wedge-shaped protrusions, an injector for inserting the injector needle into the living body and moving it forwardly and backwardly, an instrument for inserting the tissue-implantable thread into the injector, and an instrument for transforming an end of the thread to make the thread act in the living body.

According to the present trend in the plastic surgery, which is more simplified in technology and pursues a more safe method, the present invention is to remove folds more easily and safely using the opposite principle of the nose lift and fold removal, which have been performed the most to the Orientals and are achieved only by pulling tissues or pulling both sides of the thread with each other using tension of the thread.

BACKGROUND ART

The conventional rhinoplasty is performed to raise the end of the nose and lengthen a length of the nose using silicon implant, Gore-tex, autogenous cartilage, autogenous fat, and so on. However, the tissue lengthening using such materials, which have no immediate adhesion at the time of the plastic surgery, may cause a great deal of manipulations and side effects.

Particularly, many plastic surgeons do not use silicon since silicon has a very low adhesion to tissues and may cause severe problems in alien substance reaction and delayed type inflammatory reaction even though it is better in softness and bearing power than other artificial materials. In addition, Gore-tex is not good to lengthen tissues since it is not good in initial adhesion, and is difficult to raise the nose since it has a weak bearing power to compression. Moreover, the autogenous tissues are difficult to use since a patient has to endure another sacrifice in extracting tissues and it is difficult to uniformly estimate physical properties and absorptance even though they have relatively various properties.

Furthermore, all other methods excepting the fat graft provide a proof of plastic surgery since an operated person cannot freely make a "pig nose" and shake the operated nose laterally, in this instance, the pig nose and the shaking nose are greatly used by the public as methods for judging whether or not the person has been operated. On this other hand, the fat graft allows the operated person to make the pig nose but transform the nose as time goes by due to a problem of absorption, and so, needs the second plastic surgery. Moreover, the fat graft is disadvantageous in an aspect of time and in an economical aspect since surgical operations on the abdomen or the fleshy inside of the thigh must be performed to extract the tissues.

Moreover, most of the plastic surgery methods cause many troubles in daily life since they cause much swelling and take at least a week to heal.

Meanwhile, in the plastic surgery field, a thread (see FIG. 17) having a structure that wings of wedge-shaped protrusions (cogs or scales) are faced to each other on the thread has been proposed, and has been used for the fold removal or the face lifting through a skin suspension.

The thread may have a first structure consisting of two sections that the wings of the wedges are faced to each other, a second structure consisting of two sections that the wings are faced to each other and a non-wedged section formed between the two faced sections, or a third structure that use units consisting of the two faced sections and the non-wedged section formed between the two faced sections are repeatedly arranged. The thread having the third structure is used in such a way that a doctor cuts the thread as long as the necessary use unit.

The thread is used to thread folds thereto using a conventional suture needle or to smooth out the folds in such a way that one side of the thread centering around the non-wedged section is fit on an injection needle and inserted into a living body, the other side of the thread is also fit on another injection needle and inserted into the living body, and the protrusions formed at both sides of the thread generally pull drooped folds through an anchoring action. The thread allows the doctor to easily perform the plastic surgery using the needle since the thread runs through the needle while the wedge-shaped protrusions are folded without regard to any direction when the thread runs through the needle, and can secure necessary tension even though one thin thread is used since just tensile force is acted to all sections of the thread, thereby allowing a relative simple operation.

Conventional threads implanted into the living body or suture threads have been proved in their safety through a long-term use, and so, the soft tissue lengthening using the conventional thread implanted into the living body may be considered. However, the conventional thread cannot be used for anti-compression since the wings of the wedge-shaped protrusions are faced to each other, and there is no disclosure that the conventional threads were or will be used for the anti-compression.

A 3-0 Prolene suture thread with a diameter of 0.25 mm endures power of 1,200 g in connection with tension acting in a longitudinal direction, but endures no more than power of 0.1 g, which is about $1/10,000$, in connection with compression force acting in the longitudinal direction and is bent if the longitudinal compression force of more than 0.1 g is applied to the thread. Moreover, in an aspect of the structure that the wings of the protrusions are faced to each other, it is actually impossible to apply the thread to the living body since an end portion of the thread protrudes to the outside of the skin by elasticity of the human body without an action of compression to the thread when the thread is inserted into the human body. So, in an aspect of the structure, the conventional thread cannot be used for the fiber reinforced anti-compressive adherent suture method for the living body soft tissue lengthening, such as the nose lift or the fold removal performed by pushing the folds.

Due to the above reasons, the conventional rhinoplasty has a restriction in that the surgical operation method using silicon implant, Gore-tex, autogenous cartilage, autogenous fat, and so on is applied thereto in spite of many side effects and problems.

DISCLOSURE

Technical Problem

Accordingly, the present invention is to propose a new plastic surgery method and necessary instruments for making the plastic surgery enable to solve the above-mentioned problems occurring in the existing living body soft tissue lengthening method using silicon implant, Gore-tex, autogenous cartilage, autogenous fat, and so on.

For this purpose, the present invention provides a plastic surgery method, which can keep a lengthened state of living body soft tissues by morphologically transforming a suture thread proved in its safety of materials in a living body to cope with compression generated due to an action of restoring force by the living body's elasticity. Since the method is the most superior than other surgical operation methods in a clinical aspect and has a merit in that operated marks can be hidden as much as people cannot recognize the plastic surgery, the method provides excellent usefulness, and is a fiber reinforced anti-compressive adherent suture method (hereinafter, called "living body soft tissue lengthening") used to lengthen or separate the living body soft tissues.

The living body soft tissue lengthening is similar to the fold removal or the face lifting using the conventional tissue-implantable thread in an aspect that a suture thread having protrusions is used, but is different from the fold removal or the face lifting in its use purpose and uses not tension of the thread but compressive resistance force, which is the exact opposite principle. Moreover, to achieve the above object, since the protrusions must be formed in the opposite directions, it is necessary to cope with compression applied to an end of the thread to make the plastic surgery possible, and a special structure corresponding to the above is needed. Particularly, in case of the nose lifting, since the tip of the nose has many nerves sensitive to pains and the Orientals relatively greatly feel a sense of compression to the end of the thread, it is necessary to solve side effects, such as pains, exposure of the thread, inflammation, and so on, which may occur. In addition, it is necessary to consider easiness and safety of the plastic surgery since the thread having the protrusions is implanted into the living body using an injector needle.

Technical Solution

To achieve the above objects, in the present invention, the following matters were reviewed, and solutions to make a clinical use of the present invention enable are proposed.

First, the 3-0 Prolene suture thread with a diameter of 0.25 mm endures power of 1,200 g in connection with tension acting in a longitudinal direction, namely, tensile force, when the thread is 2 cm which is the shortest usable length, but endures no more than power of 0.1 g, which is about 1/10,000, in connection with power acting in the opposite direction, namely, compression force acting in the longitudinal direction and is bent if the longitudinal compression force of more than 0.1 g is applied to the thread. So, the 3-0 Prolene suture thread with a diameter of 0.25 mm is not usable theoretically.

To solve the above problem, the present invention provides a suture or tissue-implantable thread for binding living body tissues with each other, which has directionally wedge-shaped protrusions arranged in such a way that directions of power to hold tissues are opposed to each other, so that the thread separates the tissues inside the tissues, namely, lengthens the length of the tissues. In consideration of fine compression strength of each thread, several pieces of thread are used together to improve the compression strength by a mutual adhesion of the threads.

For this, the present invention provides a tissue-implantable thread, which has scale-shaped protrusions opposed to each other and formed in two different sections on one thread to form a longitudinally-acting compression force, or whose end portion is split and bent outwardly to prevent movement in a direction of the split end of the thread. Furthermore, the present invention provides a living body soft tissue lengthening to minimize compression force acting to a predetermined section of the thread by using several pieces of tissue-implantable thread together and to form a mutually supporting structure since several pieces of thread near to each other are adhered and connected with each other by the soft tissues.

Second, if the wedge-shaped protrusions are formed only in one direction, the thread may be moved and exposed to the outside of the skin since the thread is moved only in one direction in spite of a small movement like a foxtail.

To solve the above problem, the present invention provides a completed type thread having a structure that the end of the thread is split into several pieces or provides a thread having a structure that the end of the thread can be split during the surgical operation.

Third, an instrument to easily split the end of the thin thread into several pieces must be provided. So, the present invention provides a thread splitter, which can exactly split the end of the thread using a blade in a state where the end of the thread is fit thereto, and the thread splitter can be used during the surgical operation.

Fourth, since the thread must be implanted into the tissues using a needle and implanted into the tissues several times to perform the living body soft tissue lengthening, the needle must be as thin as possible. Since the needle is inserted into the tissues at least five times during once surgical operation and the insertion of the needle is carried out to the tip of the nose, which catches the eyes well, if the thickness of the needle exceeds 21 G (outer diameter of 0.85 mm), several large scars are formed on the tip of the nose, and so, it makes a practical use of the needle impossible. So, an instrument to easily insert the thread into a thin needle must be provided. For this, the present invention provides a thread insertion adaptor for helping the insertion of the thread into the conventional needle and an exclusive needle to which the thread is easily inserted. Furthermore, the present invention provides a structure that the thread is previously inserted into the needle.

Fifth, since the scale-shaped protrusions formed in the opposite directions can be expanded in their diameter to ten times when they are spread out, a structure to completely fold the protrusions formed in the opposite direction to a direction that the thread is inserted into the needle is needed. Alternately, a method that the thread, which has one-directional protrusions, is inserted into the needle and protrusions of the opposite direction or split ends are formed on the thread in a state where the protrusions of the opposite direction or the split ends are inserted into the needle must be provided and easily carried out. For this, the present invention provides a structure that protrusions are formed on the entire sections of the thread in a direction that the protrusions are folded while the thread is inserted into the needle and protrusions are formed only at an end of the thread first inserted into the needle in the opposite direction to the inserted direction of the thread to easily insert the needle or a structure that the thread, which does not have protrusions on an end of the thread first inserted into the needle, is inserted into the needle and protrusions of different directions are formed on the thread in a state where the end of the thread is exposed.

Sixth, in case where threads of various lengths must be used according to the doctor's judgment or a patient's situations, an instrument for helping the doctor to easily use them during the surgical operation must be provided. For this, the present invention provides a structure that threads of various lengths are previously mounted on the needle, and an injector, which can freely insert a needle or a thread thereto or freely adjust the inserted depth of the needle or the thread.

The present invention provides the tissue-implantable thread used for the living body soft tissue lengthening to lengthen the tissues and keep the enlarged length of the tissues by inserting the tissue-implantable thread into the human body, the adapter for mounting the tissue-implantable thread to the conventional injector needle, the thread splitter for transforming the end of the thread to help action of the thread inside the living body, and the injector moving forwardly and backwardly after the injector needle is inserted into the living body.

The tissue-implantable thread according to the present invention adopts a structure that scale-shaped protrusions are formed in two different sections of one thread in a form that the wedge-shaped protrusions are faced to each other.

The protrusions may be expressed into wedges or scales in the present invention. The protrusion includes a wedge-shaped wing and a groove split from a thread axis, and can be formed on the thread previously or later. Since the protrusions are formed in the two sections where wings of the protrusions are opposed to each other with respect to a datum point of the thread axis, the tissues are stretched without hindrance of the protrusions when the tissues are pulled and lengthened in a state where the thread is implanted into the living body, but the protrusions resist to a contraction force by the elasticity of the tissues when the pulling power is removed, and the protrusions may be modified into various forms according to the location of the datum point or a formation order of the protrusions before and after the needle is inserted into the tissues.

The fiber reinforced anti-compressive adherent suture method for the living body soft tissue lengthening according to the present invention is a surgical operation method first disclosed by the present invention. The above method can minimize compression force acting to a predetermined section of the thread by using several pieces of the tissue-implantable thread together, and keep the lengthened state of the tissues, which are artificially lengthened, without returning by their elasticity since the adjacent pieces of thread are adhered and connected with one another by the soft tissues to form a mutually supporting structure.

The tissue-implantable thread used for the above surgical operation acts in a direction to lengthen the tissues by separating the tissues inside the tissues, and adopts one of various forms to easily lengthen the tissues without resistance by the thread when the tissues are stretched after the thread is implanted into the tissues and to prevent re-contraction of the tissues since only the longitudinally-acting compression force is applied to any portion of the thread.

Advantageous Effects

The tissue-implantable thread according to the present invention is constructed of a novel protrusion-forming structure in which protrusions of two kinds acting in different directions, and does not resist to power to passively lengthen the living body but resists to power to re-contract the tissues by their elasticity in a state where the thread is implanted into the tissues, so that a compression force by the elasticity of the living body is acted without applying tensile force to any area of the thread. By the above structure, the living body soft tissue lengthening by the tissue-implantable thread is possible.

In addition, the living body soft tissue lengthening achieved by the present invention is safe and fast since the tissue-implantable thread, which is made of a suture thread material and proved in its safety, is implanted into a user's body part using an injector needle, and can overcome problems of the existing silicon Gore-tex and other materials, such as a foreign body sense. The method tried to change the form of the nose is a surgical operation method as good as you cannot find any similar technology all over the world, the most superior in a clinical aspect, and particularly, has an advantage in that plastic operation marks can be concealed.

MODE FOR INVENTION

Figure 1:
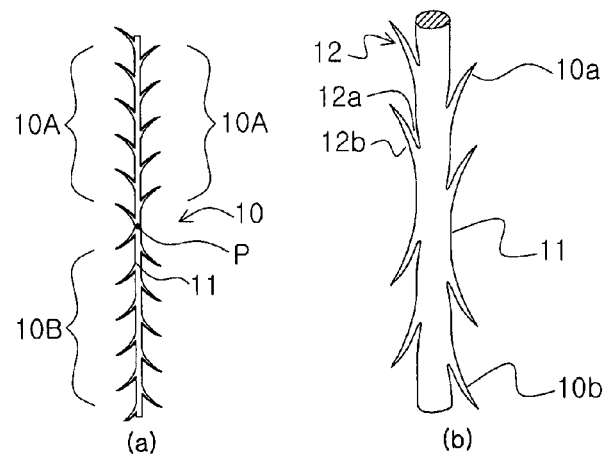
FIG. 1 is a structural view of a tissue-implantable thread according to a preferred embodiment of the present invention.

FIG. 1 illustrates a basic structure of a thread according to the present invention. The tissue-implantable thread 10 according to the present invention can be made of 3-0 Prolene, which has been used to manufacture a suture thread, or one of materials, which have been proved in biological safety. The tissue-implantable thread 10 has two sections 10A and 10B, and the two sections are arranged in such a way that scale-shaped protrusions 12 of the section 10A and scale-shaped protrusions 12 of the other section 10B are faced to each other in relation with the center of a thread axis 11, which is a datum point (P) to form compression force acting in a longitudinal direction.

The protrusion 12 takes a form similar with a form obtained when a sharp tool hacks the cylindrical thread axis 11 having the outer diameter of less than 0.6 mm to form the directional groove 12a, namely, generally takes a wedge type, concretely, a wedge-shaped scale structure, and includes a sharply protruding wing 12b and a groove 12a formed by the sharply protruding wing 12b separated from the thread axis 11. The protrusions 12 are arranged on the periphery of the thread axis 11 at fixed intervals in the form of a branch to prevent that a cross section of the thread axis 11 is excessively reduced at the groove areas, and the entire length of the thread can be standardized or about 60 mm according to an operated portion of a patient's body, or can be cut to a proper length during the plastic surgery.

Differently from the conventional thread for lifting, which pulls each section using tension thereof, since the tissue-implantable thread according to the present invention has to endure compression applied in a length direction of the thread, a bearing force is more proportional to a hardness of the thread than tensile strength of the thread, and the wings of the protrusions of the two sections are faced to each other and push tissues toward a boundary area of the two sections. That is, the tissue-implantable thread according to the present invention takes the form contrary to the conventional thread for lifting that the wings of the two sections are leaned against each other to pull each other. So, the protrusions formed on the thread must be directed not to apply power toward tensile force inside the living body. Such a form of the thread allows the thread to be moved forwardly and backwardly through a needle when the thread is inserted into the needle.

Figure 2:
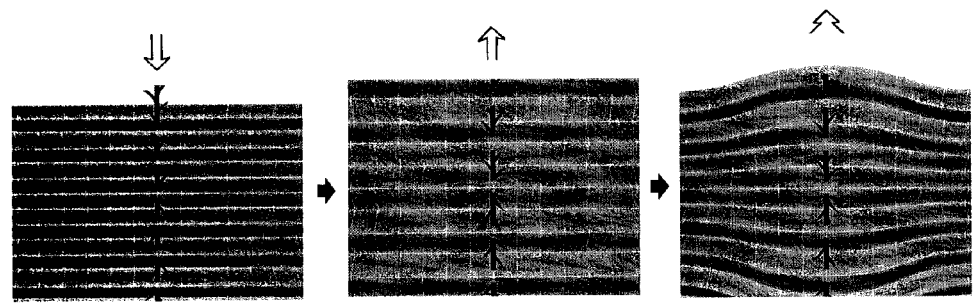
FIG. 2 is a view showing an action of the tissue-implantable thread in a living body according to the present invention.

According to the above structure, as shown in FIG. 2, the tissue-implantable thread can make tissues be easily lengthened without resistance by the thread when the tissues are stretched after the thread is implanted into the living body using the needle, and prevent that the tissues are contracted even though compression is applied by elasticity of the tissues when the lengthening power is removed, whereby the thread according to the present invention can be effectively used to raise the nose or lengthen body tissues.

The above effects can be obtained since the protrusions formed on the thread in such a way that a relative movement of the protrusions in relation with surrounding tissues is achieved only in one direction. Moreover, since the protrusions formed on one thread are formed in two sections, which have different directionalities, not tensile force but compression force is applied to the entire section of the thread.

Figure 3:
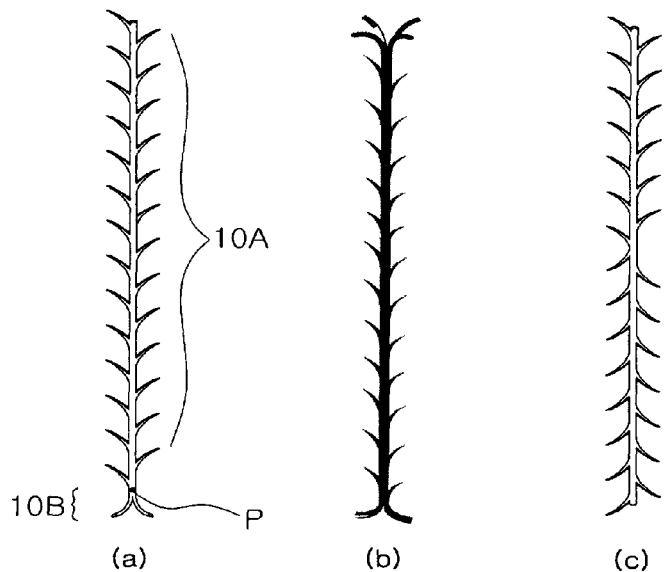
FIG. 3 is a view of a tissue-implantable thread according to a second preferred embodiment of the present invention.

Meanwhile, the structure that not tensile force but compression force is applied to the entire section of the thread can be achieved in various types including this embodiment. FIG. 3 illustrates various forms of the tissue-implantable thread according to the present invention.

FIG. 3(*a*) illustrates the tissue-implantable thread, which has two sections 10A and 10B formed on a piece of thread, the two sections 10A and 10B having scale-shaped protrusions faced to each other to form the longitudinally-acting compression force. In FIG. 3(*a*), the thread adopts a structure that the datum point (P) of the thread axis is formed on an end portion of the thread, and so, the long section has the protrusions formed on the entire section in one direction and an end of the short section is split and bent outwardly.

In the above structure of the thread, out of the two sections having different directionalities, the section deeply implanted into the human body is omitted, and the end portion of the thread is just split into several pieces, for instance, two pieces or four pieces. So, when the thread is inserted into the injector needle, if only the split end portion is inserted into the needle in a folded state, the remaining portion of the thread can be easily inserted into the needle while the wings of the protrusions of the remaining portion are folded since the wings are oppositely directed toward the insertion direction.

FIG. 3(*b*) illustrates the tissue-implantable thread, which has the datum point (F) formed at an end portion of the thread, wherein a long section has protrusions formed on the entire area thereof in one direction and a short section has an end split into at least two pieces as shown in FIG. 3(*a*), and an end of the long section is also split into at least two pieces. The above structure can prevent that the thread is exposed to the skin by preventing a movement toward the end of the thread and prevent pains by a pain-sensory organ concentrated on the skin.

The skin of the tip of the nose is sensitive to a pain and frequently moved. Furthermore, since the end of the thread receives the greatest compression at a portion nearest to the skin, a patient may feel stimulation as the skin of the tip of the nose is pricked, and occasionally, the end of the thread may pierce out the skin. So, compression applied to the thread must be dispersed at the end of the thread nearest to the skin of the tip of the nose, and in this instance, if the end of the thread having the protrusions is sharply protruded, the sharply protruding piece receives the greatest compression, and it becomes causes of the pain and exposure.

This embodiment adopts the structure that the protrusions are formed on the thread axis and the end portion of the long section is intentionally bent outwardly. The above effects can be achieved by a structure that ends of the thread are cut in such a way as to be coincided with the grooves of the protrusions as shown in FIG. 3(*c*).

The modification performed by splitting or cutting the ends of the thread may be carried out during the plastic surgery, or provided in a finished thread type.

As described above, by making the ends of the thread short or splitting the ends of the thread into several pieces, the tissue-implantable thread according to the present invention can minimize contraction pressure vertically received to the ends of the thread, and prevent the needle-pricking-like pain and prevent the exposure of the thread through a dispersion of pressure.

Figure 4:
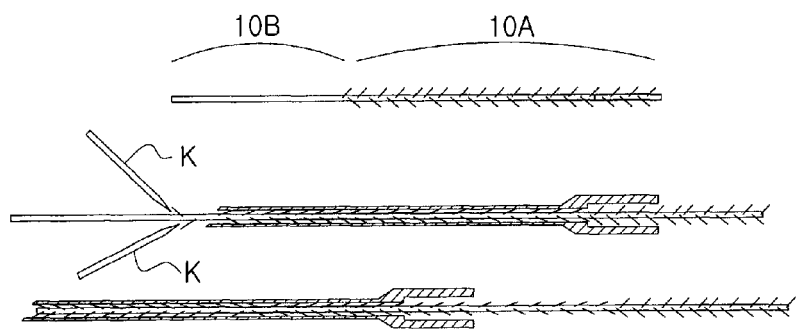
FIG. 4 is a view of a tissue-implantable thread according to a third preferred embodiment of the present invention.

In stead of the structure that the scale-shaped protrusions are formed in the two sections 10A and 10B formed on a piece of thread and the protrusions of the two sections are faced to each other to form the longitudinally-acting compression force, FIG. 4 illustrates a structure of the thread that the protrusions are formed just on one section, which is not hindered in insertion of the injector needle, and the remaining section may have protrusions, which will be made by a knife (K) after the thread is inserted into the injector needle.

According to the above structure, a doctor inserts the thread into a thin needle of less than 21 G in a state where the protrusions are folded without using additional tools, and pulls the thread into the needle while forming protrusions in the opposite direction to the previously formed protrusions using the knife in a state where the section, which does not have the protrusions, is exposed from an end of the needle.

Figure 5:
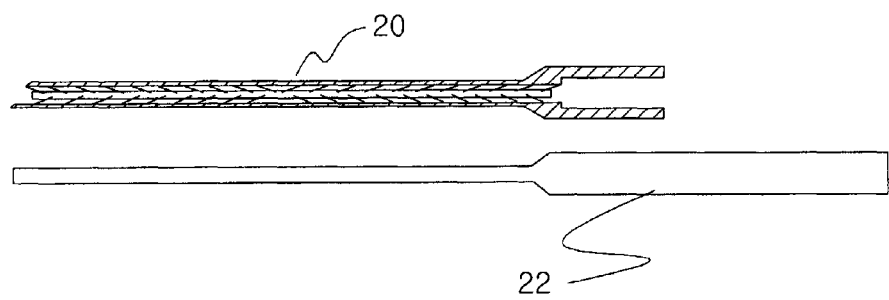
FIG. 5 is a view showing a structure that the tissue-implantable thread according to the present invention and a needle are formed integrally with each other.

FIG. 5 illustrates a state where the thread according to the present invention is previously inserted into the needle 20.

Figure 6:
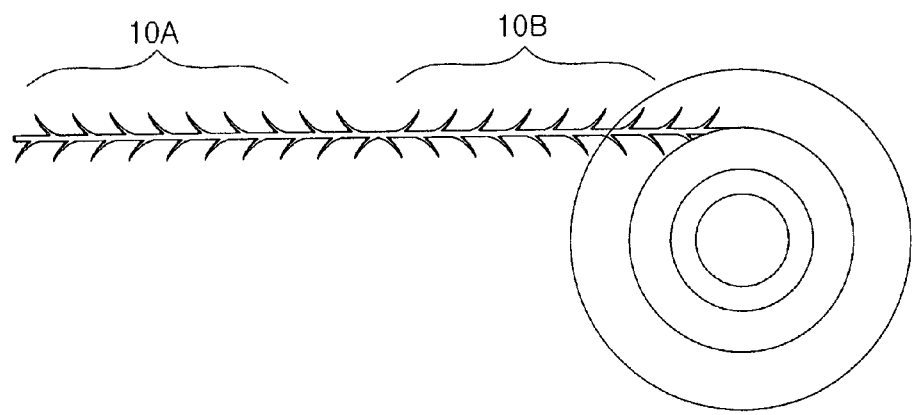
FIG. 6 is a view showing a roll type tissue-implantable thread according to the present invention.

In this embodiment, the needle may have various lengths and standards, but in consideration that it is used for an aesthetic purpose, a needle of less than 21 G, which does not cause a scar, is used. The needle has the inner diameter formed in such a way as to form an interval of about 0.1 mm between the inner diameter and the thread, and the thread inserted into the needle can be extracted out while being pushed forwardly using a core 22, which can pass through a needle eye. FIG. 6 illustrates a form that a use unit, in which two sections having wings of protrusions are faced to each other, is repeated. The use unit can be repeatedly formed in various ways within a range of 1 cm to 6 cm, and the thread is provided in a form that it is rolled on a roll, and can be cut by the use unit as long as the doctor wants to use.

So, the thread having the above structure can be used properly to an operated portion of the patient's body since the thread having the use units continuously formed is cut as long as a necessary use unit and both ends of the cut thread are cut out properly to the length of the operated portion of the patient's body.

Figure 7:
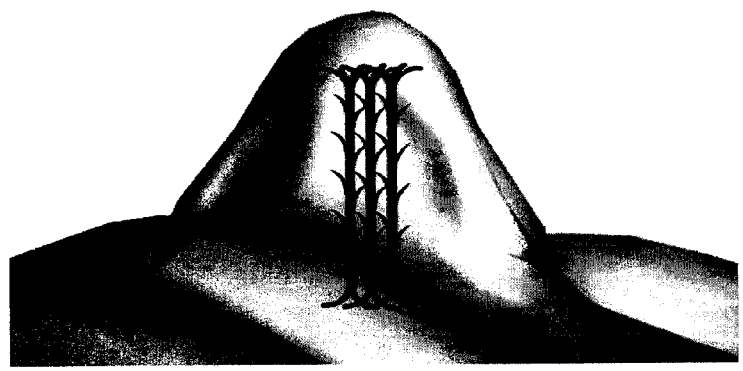
FIG. 7 is a view showing a state where the tissue-implantable thread according to the present invention is applied to the soft tissue lengthening.

FIG. 7 illustrates a state where several pieces of thread are concentratively inserted to apply compression force to each piece of thread. FIG. 7 shows that the basic concept of the living body soft tissue lengthening is to keep a lengthened state of the living body tissues by providing a still more reinforced resistance strength by an adhesion phenomenon and a focusing effect, which occur when the wings of the protrusions are tangled with each other, than a piece of thread.

The thickness and surgical operation intervals of the thread according to the present invention may be varied according to elasticity of the lengthened portion, but in case of the general nose lift, 3 to 10 threads of about 0.4 mm in thickness are inserted within a diameter of about 5 mm using a 21 Gauge needle, which does not show inserted marks to the outside.

A thin needle must be used if possible since the thread must be implanted into the tissues in a state where it is inserted into the needle and inserted several times at one region. In this instance, since the needle is inserted into the tissues at least five times during once plastic surgery and inserted into the tip of the nose, which is conspicuous, if the thickness of the needle exceeds 21 G (outer diameter of 0.85 mm), it is impossible to use it practically due to a scar. So, if possible, the thin thread and needle must been used within a permitable range of the resistance strength to compression, and for this, a tool for easily inserting the thread into the needle must be provided or the thread must be provided in a state where the thread is previously inserted into the needle.

In the present invention, the thread is inserted into the needle on the spot. In the state where the protrusions are formed on the thread axis in the opposite directions, it is very difficult to insert the thread into the needle since the thread is inserted into the needle while the protrusions of the section first inserted into the needle are spread out and so the outer diameter is expanded to about ten times. To overcome the above problem, the present invention proposes n adapter or an exclusive injector needle for easily inserting the thread into the needle.

Figure 8:
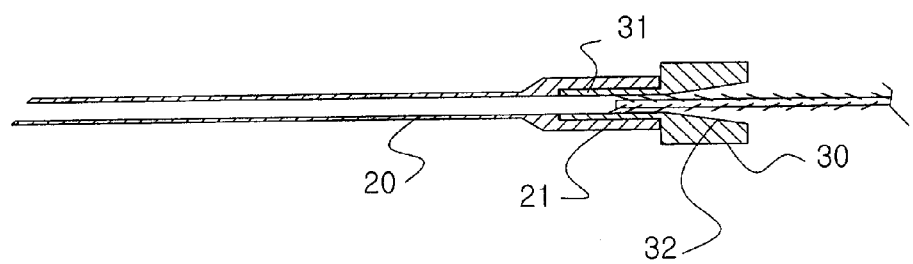
FIG. 8 is a view showing an adapter to insert the tissue-implantable thread into an injector needle.

FIG. 8 illustrates a preferred embodiment of the adapter 30 for inserting the thread into the needle. The adapter 30 includes a side end 31 inserted into a hub 21 of a conventional needle 20, and an inner tapered portion 32 formed at the center thereof, the inner tapered portion 32 having a diameter starting with the same diameter as the needle but gradually increasing toward the outer side end.

The conventional injector needle is suddenly tapered in the inner smallest diameter area of the injector needle of the hub since the needle is formed to insert the thread thereto, and so, it is difficult to insert the thread into the needle since the protrusions of the thread are caught to the tapered portion or a rough portion of the end portion of the thread is caught to the tapered portion. To solve the above problem, the adapter according to the present invention has a smoother inner tapered portion, and so, the rough portions can be slid and enter the smallest inner diameter, which is the same as the inner diameter of the needle, while the protrusions are naturally folded according to the progress of the thread. Moreover, since the outer form of the adapter is coincided with the hub of the conventional injector needle, the center of the smallest inner diameter is coincided with the center of the smallest inner diameter of the injector needle.

By the above structure, the adapter 30 for inserting the thread into the needle allows the doctor or an assistant to easily insert the thread into the needle since the thread is inserted into the expanded inner tapered portion after the adapter 30 is fit to the hub of the conventional injector needle, and to insert the tissue-implantable thread of the present invention, which has the wings of the protrusions formed in the opposite directions, into the needle by pushing the thread into the needle while folding the wings using forceps if the wings is directed toward the insertion direction.

Figure 9:
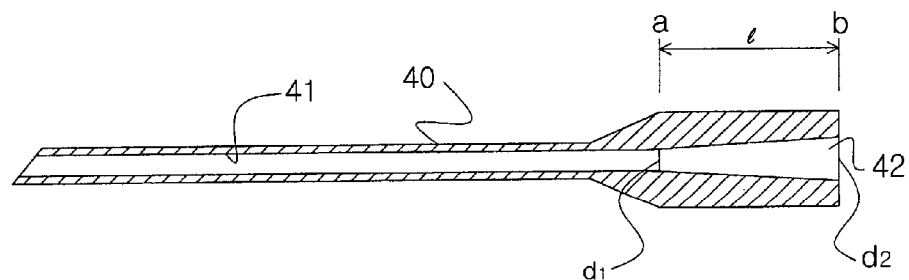
FIG. 9 is a view showing the injector needle configured in such a way as to use the tissue-implantable thread according to the present invention thereto.

FIG. 9 illustrates the exclusive needle 40 for easily implanting the thread into the living body. For this, the exclusive needle 40 has the same outward appearance as the conventional injector needle, and includes a hole 41 formed at the center thereof and having the inner diameter of less than 0.5 mm to insert the thread having the protrusions thereto, and a tapered entrance 42 of a smooth trumpet shape, which has the shortest distance (l) ranging from a position of the smallest inner diameter (d1) to a portion having the inner diameter of 1 mm (d2) exceeds at least 4 mm.

Since the needle having the small outer diameter can prevent damages and scars of the tissues and induce the protrusions of the thread to be guided by the tapered entrance and naturally inserted, the needle according to the present invention can considerably reduce a time period taken to insert a piece of short thread into the needle several times.

The present invention proposes a thread splitter for exactly splitting an end of the thread during the plastic surgery.

The thread splitter 50 includes a space or groove for inserting a blade therein to correctly locate the blade at a fixed portion of the thread to cut the end of the thin thread, the blade being in contact with the thread when the blade enters along the space, a movable guide having a guide groove for putting the blade thereon when the blade is inserted there to while cutting the thread, and a thread fixing structure for preventing movement of the thread during cutting the thread.

Moreover, according to another structure of the thread splitter 50, without guiding the thread in a state where the blade is in a direct contact with the thread during a process that the blade approaches the thread, the blade is mounted on a body having a specific shape, and the body is inserted into a guide having a shape corresponding to the outer wall shape of the body to guide the body and formed around the thread fixing structure, so that the blade mounted on the body can cut the thread in a longitudinal direction when the body is inserted into the guide.

Figure 10:
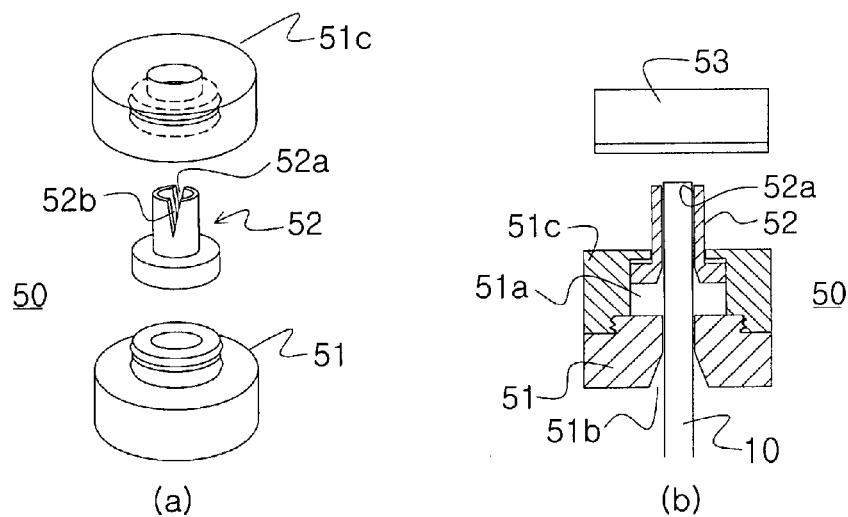
FIGS. 10 to 12 are views showing a tissue-implantable thread splitter for dividing an end of the tissue-implantable thread according to the present invention.

FIG. 10 illustrates a preferred embodiment of the thread splitter 50. The thread splitter 50 includes the body 51, the guide 52 coupled to the body 51, and a thin blade 53 for splitting the end of the thread. The body 51 includes a gap 51c coupled to the upper center of the body 51 to form a guide insertion space 51a of a restricted length for inserting the guide 52 thereto and vertically moving the inserted guide 52. The guide 52 inserted into the guide insertion space 51a includes a through-hole 52a formed at the center thereof for forcedly fitting and passing the thread 10 and a wedge-shaped guide groove 52b formed on the front and rear of the guide for guiding the blade. The body 51 further includes a thread insertion groove 51b formed at the center thereof for forcedly fitting the thread thereto and guiding the thread to the through-hole of the guide.

According to the above structure of the thread splitter 50, in a state where the thread is inserted into the splitter through the thread insertion groove 51b of the body and drawn to a position of the guide groove, the thread splitter splits the inside thread by applying power after the blade is fit to the guide groove 52b, or splits the end of the thread by pushing upwardly the guide in a state where the blade is in contact with the guide groove, so that the thread splitter can bisect the thread into two equal parts or divide the bisected thread into four equal parts and freely adjust a split depth using a protruding height of the thread or a movement distance of the guide.

Figure 11:
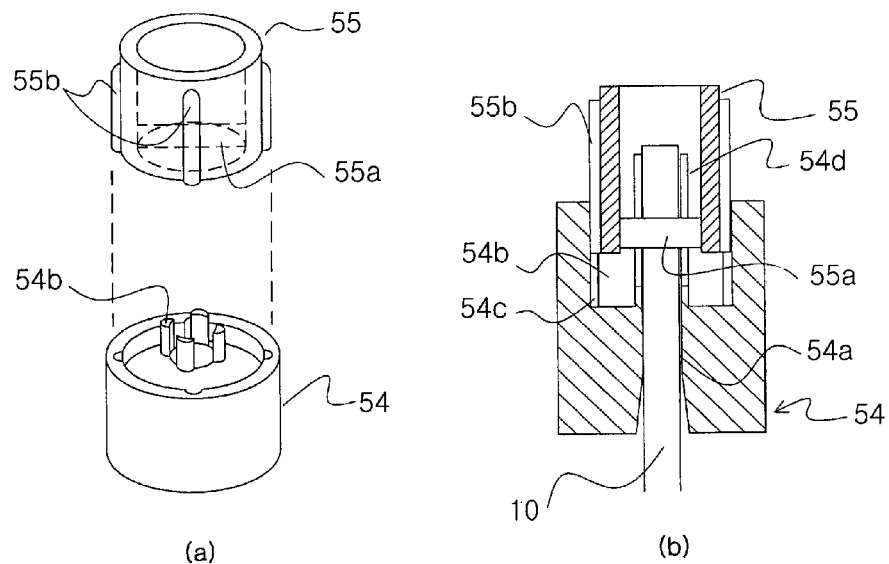

FIG. 11 illustrates another preferred embodiment of the thread splitter. The thread splitter includes a body 54 and a blade rod 55 inserted into the upper portion of the body and having a blade 55a formed in the lower end portion thereof in such a way as to split the center thereof. The body 54 includes a thread insertion hole 54a formed at the central portion thereof to insert and fix the thread thereto, movable grooves 54b and guide grooves 54c extending from the top portion of the thread insertion hole 54a to the upper end of the body 54, and support rods 54d of an elastic bar type formed on an extension line of the thread insertion hole 54a for fixing and holding the thread. The blade rod 55 includes the blade 55a cylindrically formed inside the lower end thereof, and guides 55b formed on the outer peripheral surface thereof and being vertically movable in a state where the guides 55b are coupled with the movable grooves 54b.

When the thread is inserted to the thread fixing hole of the body 54 and pushed to the support rods, the support rods fix the thread by their elasticity like the support rods wrap the thread, and so, the thread splitter can split the end of the thread to a necessary depth by pushing the blade rod into the movable groove in the above state.

In the present invention has four support rods and four guides formed on the blade rod and four guide grooves to make a match, so that the thread can be split into four pieces when the blade rod split the thread while rotating at angles of 90°.

Figure 12:
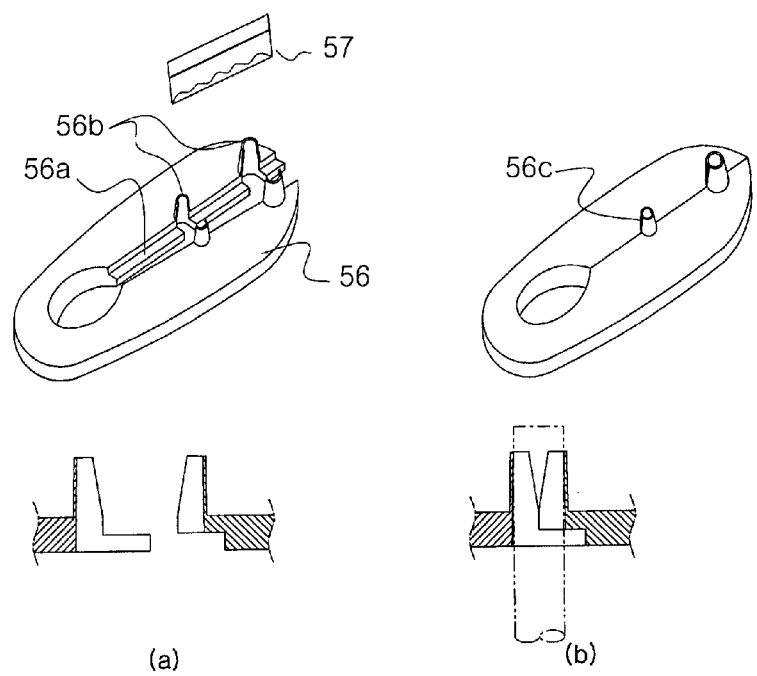

FIG. 12 illustrates forceps 56 made of an elastic material as another embodiment of the thread splitter according to the present invention. Blades of the forceps 56 are engaged with each other in a structure of a fitting jaw 56a, and at least one holder 56b having different diameters is formed on the blade of the forceps for biting the thread.

Each holder is in a semi-cylindrical form belonging to each blade and has the inner diameter gradually reduced toward the top thereof, so that the upper end portion presses and fixes the thread in a state where two blades engage with each other when the thread 10 is inserted to the holder and the two blades are pressed. Moreover, the holder has a gap 56c formed on the engaging portion thereof to split the thread using a blade 57 in a state where the thread is forcedly fixed.

Since the thread splitter adopts the forceps structure, it can easily fix the thread, correctly fix the thread by the engaging jaw, and exactly split the end of the thread by guiding the blade through the gap.

The thread splitter according to this embodiment can prevent movement of the end of the thread implanted into the living body and prevent exposure of the thread to the outside of the skin and a foreign body sense by splitting the end of the thread to be located at the cuticle before the thread is inserted into the injector needle or by splitting the end of the thread in a state where the end of the thread passing through the end of the injector needle is drawn out more.

To implant the thread into the living body, an injector having a structure to forwardly and backwardly move the thread through the needle or forwardly and backwardly move the needle without regard to the thread can be used very effectively.

Figure 13:
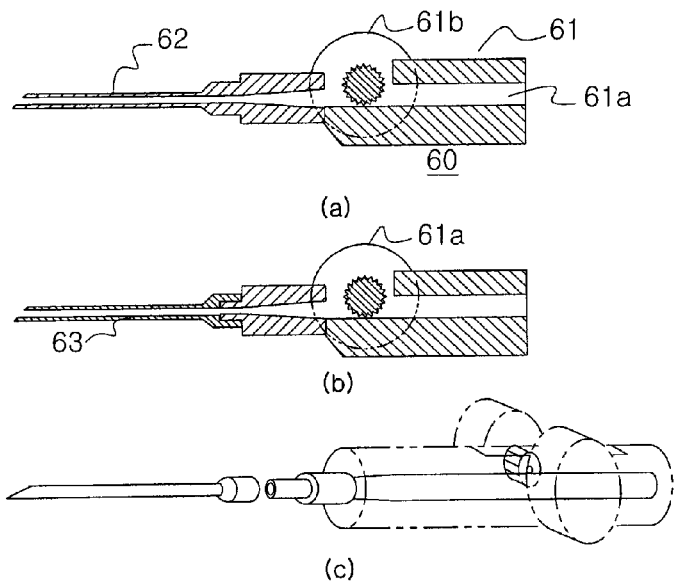
FIGS. 13 and 14 are views showing an injector for implanting the tissue-implantable thread into the living body according to the present invention.

FIG. 13 illustrates a preferred embodiment of an injector 60 for inserting the thread to the needle. The injector 60 includes an injector body 61 having a passageway 61a formed inside the injector body 61 for passing the thread therethrough and a roller 61b formed on the passageway 61a for pressing and advancing the thread. The injector 60 may adopt a structure (a) having an injector needle 62 formed integrally with a thread drawing 61c of the passageway 61a or a structure (b) that the conventional injector needle 63 is coupled to the thread drawing 61c.

The injector is disposable in case of the former structure, but reusable by replacing the injector needle with a new one in case of the latter structure. In case of the latter structure, the thread drawing is fit to the hub of the injector needle, and the passageway of the thread drawing is tapered so that the thread can be smoothly introduced and moved into the injector needle by pressing of the roller.

Figure 14:
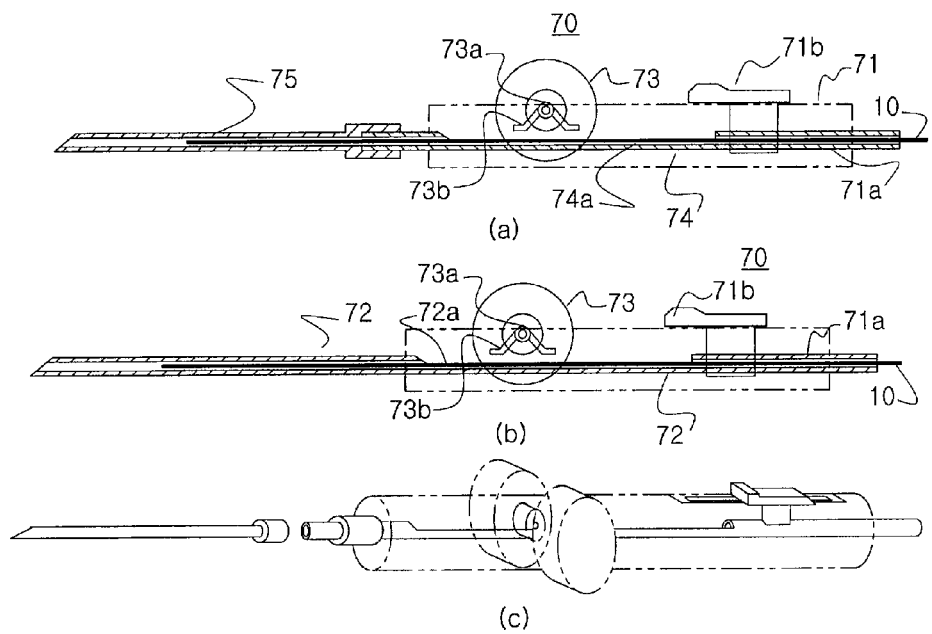

FIG. 14 illustrates an injector, which allows movement of the thread inside the injector needle and back and forth movements of the injector needle inside the injector body, according to another embodiment.

The injector is configured into a structure (a) including an injector body 71 formed in a hand-grip type and having a passageway 71a formed inside the injector body 71, an injector needle 72 inserted into the passageway 71a, and a roller 73 coupled to the passageway 71a of the injector body 71. The injector needle 72 includes a body portion 72a exposed to the outside of the injector body 71 and coupled to a push stick 71b slidably combined to the injector body 71 to thereby move forwardly and backwardly by the push stick 71b. A portion of the body portion 72a of the injector needle 72 located on the injector body 71 is opened upwardly, so that the inserted thread is exposed from the injector body. The roller 73 coupled to the passageway 71a of the injector body 71 includes a shaft 73a and a spring for supporting the shaft 73a to thereby be in contact with and press out the thread exposed from the opened portion of the injector needle only in a pressed state.

The above embodiment shows the structure, that the injector and the injector needle are formed integrally with each other, for using the disposable injector needle, but a structure that the conventional injector needle can be used and replaced with a new one is also possible.

FIG. 14(b) illustrates the structure that the injector needle can be replaced with a new one. Referring to FIG. 14(b), the injector includes a separate sliding bar 74 for separating a portion located on the body portion of the injector needle from the injector needle and inserting the thread into the body portion. A body portion 74a of the sliding bar 74 is exposed to the outside of the injector body 71 and coupled to the push stick 71b slidably coupled to the injector body, whereby the sliding bar 74 moves forwardly and backwardly inside the injector body by the push stick 71b and a portion of the body portion 74a of the sliding bar 74 is opened upwardly to expose the inserted thread to the outside of the injector body. A roller 73 is coupled to the passageway 71a of the injector body 71, and includes a shaft 73a and a spring for supporting the shaft 73a to thereby be in contact with and press out the thread exposed from the opened portion of the injector needle only in a pressed. The front-end portion of the sliding bar protrudes from the injector body, and the hub of the injector needle 75 can be fit to the front-end portion of the sliding bar.

Since the injector having the above structure allows the back and forth movement of the thread inside the injector needle and the back and forth movement of the injector needle inside the injector in a state where the thread is inserted into the injector needle, whereby the doctor can perform plastic surgery while selecting an inserted depth or location of the thread according to the doctor's intention.

The above instruments can be effectively used to perform the human body lengthening such as the nose lift, and provide a merit that the doctor can apply a proper method on the spot under the doctor's judgment according to various characteristics of operated regions or patients.

The plastic surgery process using the thread and instruments according to the present invention will be described in detail.

① In Case of Thread Integrated with Injector Needle

The thread integrated with the injector needle is the easiest to use and can reduce a surgical operation period. The thread with the length of 1 cm to 6 cm adopting various forms is manufactured in the form that the thread is inserted into the exclusive injector needle with the thickness of less than 21 G or the conventional injector needle.

The doctor inserts the needle into wanted tissues to be lengthened, and leaves the thread after pulling out the injector needle while pushing the thread with the push stick. After that, the doctor sufficiently lengthens the tissues with the hand and takes off the hand. Then, the thread acts to keep the lengthened length by the protrusions of the two sections opposed to each other. At strongly elastic area of the tissues, several pieces of thread are inserted into the elastic area to overcome the elasticity.

The above surgical operation can considerably reduce the operation period since the previously completed thread is used.

② Method to Perform Plastic Surgery while Combining the Previously Completed Thread to Injector Needle The doctor selects the thread with a necessary length from the completed threads with various forms and lengths, and inserts and uses the thread to the exclusive needle or to the conventional injector needle on the spot using the adapter for inserting the thread to the needle, and the process to insert the needle into the living body is the same as the above.

The doctor can easily select the thread of a wanted length since the above method allows the doctor to select the length of the thread after the needle is inserted into the tissues, and the manufacturing costs drops since the injector needle is reusable to the same patient.

③ Method to Use Thread Having Single-directional Protrusions

The thread having only the single-directional protrusions can be easily inserted into the needle with the thickness of less than 21 G on the spot. After inserting the thread into a wanted needle to go according to the direction of the protrusions, when the end of the thread goes out through an opposite entrance of the needle, the doctor stops the advance of the thread before the protrusions are exposed. After that, the doctor forms a protrusion on the end of the exposed thread using a blade or splits the thread into several pieces using the thread splitter and retreats the split thread to hide the thread into the needle. After that, the doctor inserts the needle into the tissues, and then, removes the needle by retreating only the needle. After that, the doctor cuts the thread exposed to the outside of the skin after leaving the thread of just several millimeters, cuts the end of the exposed thread up to a position of the groove of the protrusion to transform the thread, and then, pulls the tissues, so that the end of the transformed thread is pushed and buried into the skin. As described above, to transform the thread on the spot, some section of the thread shall not have the protrusions formed previously.

This method has several advantages in that manufacturing costs can be reduced since a manufacturing process of the thread is simple and in that the doctor can easily select the length of the thread and it is economic in an aspect of consumption of the thread since the doctor can cut and use the thread as long as it is needed. However, this method has a disadvantage in that it takes much time for the doctor to directly transform the end of the thread on the spot.

Figure 15:
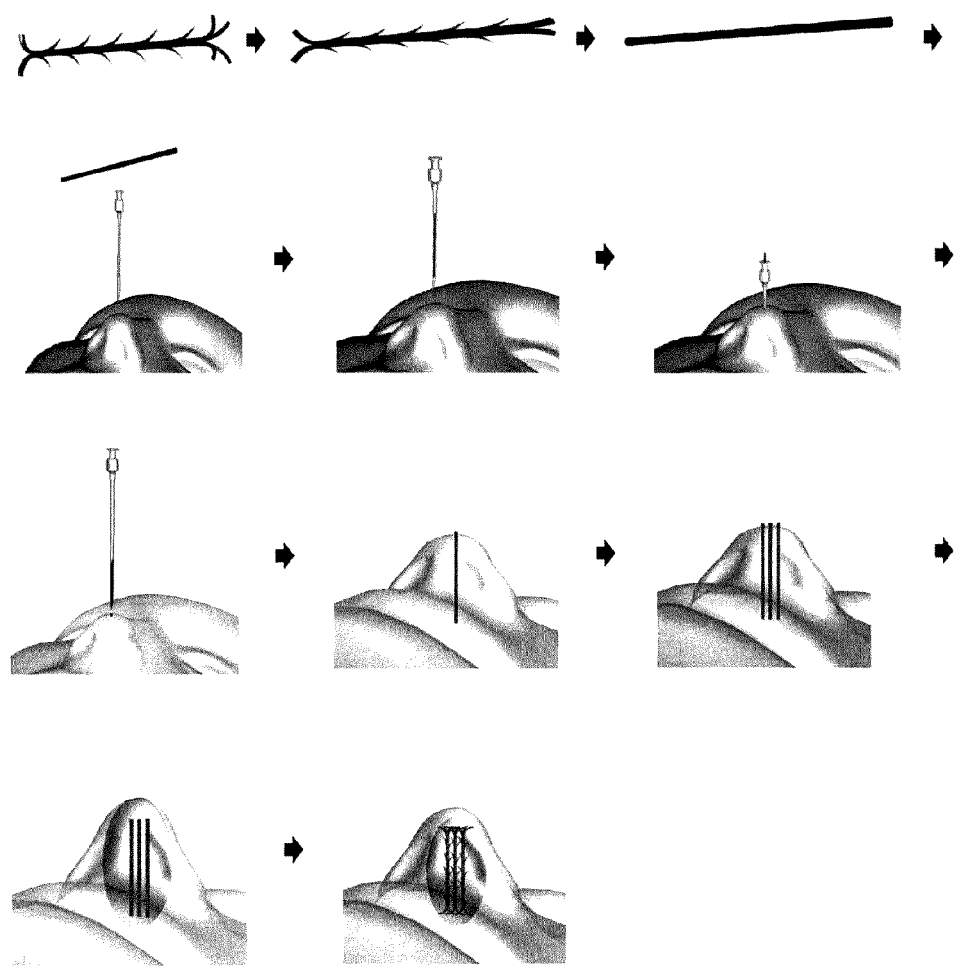
FIG. 15 is a view showing a state where the tissue-implantable thread according to the present invention is applied to the nose lift.

FIG. 15 illustrates a state where the thread having the structure that protrusions are formed in one direction and both ends of the thread are split into several pieces is applied to the nose lift. In this instance, the thread may be inserted into the injector or provided in the form that the thread is previously inserted into the injector.

After the thread is inserted into the injector needle or in a state where the thread is previously inserted into the injector, the doctor inserts the injector needle to a wanted tissue area to be lengthened, and pushes out the thread inserted into the injector needle using a core to expose the end of the thread to the outside of the skin, and then inserts the thread according to the present invention after pulling out the needle. After repeating the above process several times, the doctor pulls the tip of the nose, and then, the end of the thread is pulled and buried into the skin.

In the above state, the several pieces of inserted thread are adhered with each other due to the directionality and the wedge action of the protrusions formed on the thread, and so, the thread keeps the lengthened state in opposition to the contraction by elasticity of the nose.

Figure 16:
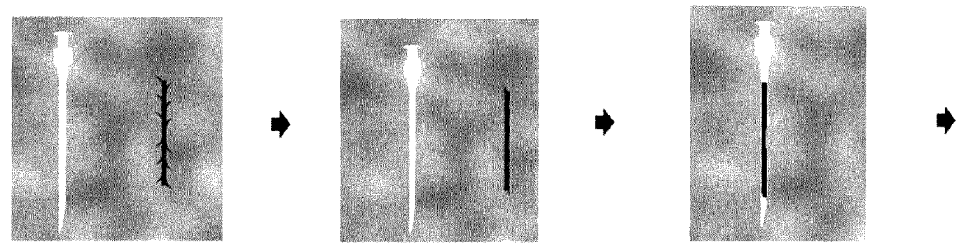
FIG. 16 is a view showing a state where the tissue-implantable thread according to the present invention is applied to a surgical operation to smooth out folds.
Figure 16:
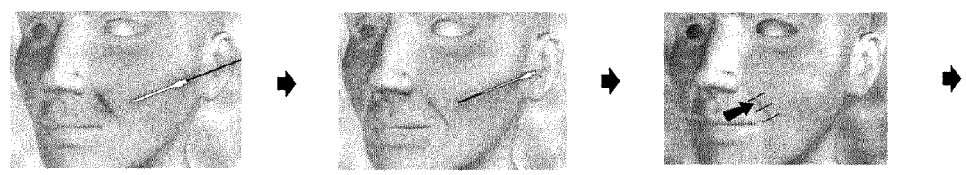
Figure 16:
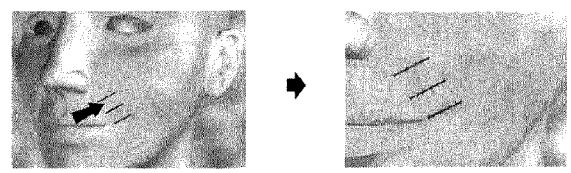
Figure 17:
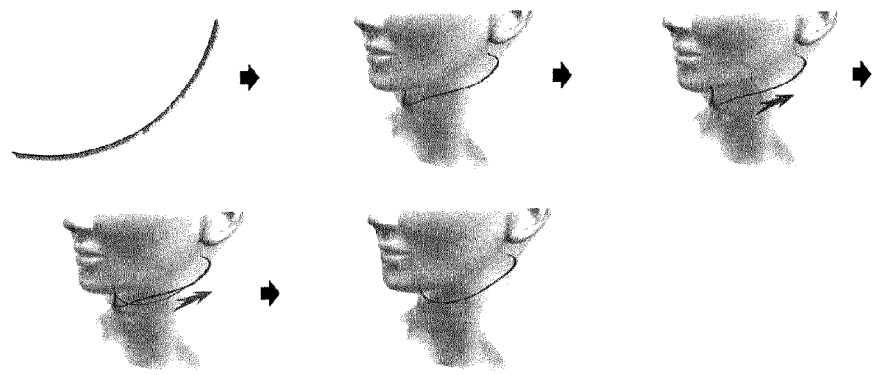
FIG. 17 illustrates a conventional thread for lifting and its used state.

FIG. 16 illustrates another example of the plastic surgery using the present invention, wherein the present invention is applied to the plastic surgery to fold out drooped folds on the face.

The present invention proposes the first living body soft tissue lengthening using several pieces of conventional suture threads, which have been proved in their safety and are frequently used, to secure bearing force necessary for lengthening the soft tissues through anti-compression by mutual adhesion of the threads. In the present invention, the tissue-implantable thread according to the present invention is an essential part enabling the living body soft tissue lengthening, and the adapter, the exclusive injector, the needle and the thread splitter proposed by the present invention are essentially necessary to perform the living body soft tissue lengthening and belong to the same category as the thread.

INDUSTRIAL APPLICABILITY

As described above, the present invention is to provide instruments necessary for the surgical operation performed to keep the length of the lengthened tissues, for instance, a raised nose on the face, using the improved thread implanted in the living body, more particularly, to provide instruments for a fiber reinforced anti-compressive adherent suture method used to lengthen or separate soft tissues in the living body, which includes a tissue-implantable thread having wedge-shaped protrusions, an injector for inserting the injector needle into the living body and moving it forwardly and backwardly, an instrument for inserting the tissue-implantable thread into the injector, and an instrument for transforming an end of the thread to make the thread act in the living body.

According to the present trend in the plastic surgery, which is more simplified in technology and pursues a more safe method, the present invention is to remove folds more easily and safely using the opposite principle of the nose lift and fold removal, which have been performed the most to the Orientals and are achieved only by pulling tissues or pulling both sides of the thread with each other using tension of the thread.

The invention claimed is:

1. An injector for injecting a tissue-implantable thread into a living body,
   wherein the tissue-implantable thread is used in fiber reinforced anti-compressive adherent suture method for living body soft tissue lengthening, the tissue-implantable thread having protrusions with directionality used to lengthen an area of the human body, wherein the protrusion includes a sharply protruding wing obtained when a sharp tool hacks the cylindrical thread axis and having a wedge-shaped scale structure and a groove formed by the sharply protruding wing separated from the thread axis, the protrusions being formed in two sections in such a way that tapered ends of the wings formed in one section are faced to and lean their back against tapered ends of the wings formed in the other section with respect to a datum point formed on a thread axis of the thread, wherein the thread is implanted into a living body by an injector needle, whereby tissues are stretched without hindrance of the wings when the tissues are pulled to be lengthened in a state where the thread is implanted into the living body but the protrusions resist to a re-contraction force by elasticity of the tissues when the pulling force is removed, wherein one end portion or each of both end portions of the thread is split into at least two pieces, wherein the injector comprises an injector body formed in a hand-grip type and having a passageway formed inside the injector body for passing an injector needle therethrough, an injector needle inserted into the passageway, a push stick slidably coupled to the body, a body portion of the injector needle being exposed to the outside of the injector body and coupled to the push stick to thereby move forwardly and backwardly by the push stick, a portion of the body portion of the injector needle coupled to the injector body being opened upwardly to expose the inserted thread from the injector body, and a roller combined to the passageway formed inside the injector body, the roller having a shaft supported by a spring to thereby be in contact with and press out the thread exposed from the opened portion of the injector needle only in a pressed state.

2. The tissue-implantable thread according to claim 1, wherein the datum point is formed at the center of the thread axis, and the two sections are formed in such a way that the tapered portions of the wings of the protrusions are directed toward ends of each side of the entire thread and the wings formed in one section lean their back against the wings formed in the other section, but the grooves of the protrusions formed in one section face the grooves of the protrusions formed in the other section at a position of the thread axis.

3. The tissue-implantable thread according to claim 1, wherein the datum point is formed at the center of the thread axis, and the two sections are formed in such a way that the wings of the protrusions formed in one section are opposed to the wings of the protrusions formed in the other section, and in this instance, protrusions of one of the two sections are formed after the thread is inserted into a needle.

4. An injector for injecting the tissue-implantable thread into a living body, wherein the tissue-implantable thread is used in fiber reinforced anti-compressive adherent suture method for living body soft tissue lengthening, the tissue-implantable thread having protrusions with directionality used to lengthen an area of the human body, wherein the protrusion includes a sharply protruding wing obtained when a sharp tool hacks the cylindrical thread axis and having a wedge-shaped scale structure and a groove formed by the sharply protruding wing separated from the thread axis, the protrusions being formed in two sections in such a way that tapered ends of the wings formed in one section are faced to and lean their back against tapered ends of the wings formed in the other section with respect to a datum point formed on a thread axis of the thread, wherein the thread is implanted into a living body by an injector needle, whereby tissues are stretched without hindrance of the wings when the tissues are pulled to be lengthened in a state where the thread is implanted into the living body but the protrusions resist to a re-contraction force by elasticity of the tissues when the pulling force is removed, wherein one end portion or each of both end portions of the thread is split into at least two pieces, wherein the injector comprises an injector body formed in a hand-grip type and having a passageway formed inside the injector body for passing an injector needle therethrough, a sliding bar combined to the passageway for inserting the thread thereto, a push stick slidably coupled to the body, a body portion of the sliding bar being exposed to the outside of the injector body and coupled to the push stick to thereby move forwardly and backwardly inside the injector body by the push stick, a portion of the body portion of the sliding bar being opened upwardly to expose the inserted thread from the injector body, and a roller combined to the passageway formed inside the injector body, the roller having a shaft supported by a spring to thereby be in contact with and press out the thread exposed from the opened portion of the injector needle only in a pressed state.

5. The tissue-implantable thread according to claim 4, wherein the datum point is formed at the center of the thread axis, and the two sections are formed in such a way that the tapered portions of the wings of the protrusions are directed toward ends of each side of the entire thread and the wings formed in one section lean their back against the wings formed in the other section, but the grooves of the protrusions formed in one section face the grooves of the protrusions formed in the other section at a position of the thread axis.

6. The tissue-implantable thread according to claim 4, wherein the datum point is formed at the center of the thread axis, and the two sections are formed in such a way that the wings of the protrusions formed in one section are opposed to the wings of the protrusions formed in the other section, and in this instance, protrusions of one of the two sections are formed after the thread is inserted into a needle.

* * * * *